(12) United States Patent
Sharma

(10) Patent No.: US 12,704,246 B2
(45) Date of Patent: Aug. 11, 2026

(54) FAUCET ILLUMINATION

(71) Applicant: Sensor Electronic Technology, Inc., Columbia, SC (US)

(72) Inventor: Piyush Sharma, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 19/268,043

(22) Filed: Jul. 14, 2025

(65) Prior Publication Data

US 2026/0022832 A1 Jan. 22, 2026

Related U.S. Application Data

(60) Provisional application No. 63/673,811, filed on Jul. 22, 2024.

(51) Int. Cl.

| | |
|---|---|
| ***F21V 33/00*** | (2006.01) |
| ***A61L 2/10*** | (2006.01) |
| ***F21S 8/00*** | (2006.01) |
| ***F21V 23/04*** | (2006.01) |
| ***F21Y 113/00*** | (2016.01) |
| *A61L 103/05* | (2026.01) |
| *F21Y 107/30* | (2016.01) |
| *F21Y 113/13* | (2016.01) |

(52) U.S. Cl.
CPC .............. *F21V 33/004* (2013.01); *A61L 2/10* (2013.01); *F21S 8/03* (2013.01); *F21V 23/0464* (2013.01); *F21V 23/0471* (2013.01); *A61L 2103/05* (2026.01); *A61L 2202/11* (2013.01); *A61L 2202/17* (2013.01); *F21Y 2107/30* (2016.08); *F21Y 2113/13* (2016.08); *F21Y 2113/30* (2023.05)

(58) Field of Classification Search
CPC ............... F21V 33/004; F21V 23/0471; F21V 23/0442; F21V 23/0464; F21W 2121/02; F21W 2131/30; F21W 2131/301; F21S 10/002; F21Y 113/00
See application file for complete search history.

(56) References Cited

U.S. PATENT DOCUMENTS

| | | | | |
|---|---|---|---|---|
| 10,458,642 | B2 * | 10/2019 | Heuer ..................... | F21S 10/02 |
| 2005/0276035 | A1 * | 12/2005 | Currie .................. | F21V 33/004 362/96 |
| 2014/0261767 | A1 * | 9/2014 | DeVries ................ | E03C 1/0401 174/138 R |

* cited by examiner

*Primary Examiner* — William J Carter
(74) *Attorney, Agent, or Firm* — LaBatt, LLC

(57) ABSTRACT

Mounting hardware for a faucet including one or more light sources for illumination. The light source(s) can be configured to emit light from one or more vertically oriented surfaces of the mounting hardware. One or more sensors can acquire sensor data that can be used to control operation of the light source(s). The light sources can include visible and/or ultraviolet light sources. When included, the ultraviolet light can be directed onto one or more areas of one or more horizontally oriented surfaces located adjacent to the vertically oriented surface(s). The light sources can be located in an escutcheon of the mounting hardware.

20 Claims, 7 Drawing Sheets

FAUCET ILLUMINATION

REFERENCE TO RELATED APPLICATIONS

The current application claims the benefit of U.S. Provisional Application No. 63/673,811, filed on 22 Jul. 2024, which is hereby incorporated by reference.

TECHNICAL FIELD

The disclosure relates generally to illuminating and/or treating an area around a faucet, and more particularly, to a solution for illuminating and/or preventing mold growth in the area.

BACKGROUND ART

Currently, water faucet design is driven by a combination of functionality, aesthetics, and water conservation. Traditional faucet designs are engineered to efficiently deliver water while complementing the overall aesthetic of the room and corresponding fixtures, such as a kitchen or a bathroom. Despite advancements in materials and manufacturing processes, a persistent challenge remains, the propensity for mold and bacterial growth in and around horizontal surfaces around the faucet, such as around the interface between the faucet and the countertop.

This issue arises due to the intricate geometry of the faucet mounting interface, which often creates small crevices and gaps where water can accumulate and stagnate. Over time, this stagnant water provides an ideal breeding ground for mold and bacteria, posing significant hygiene concerns for users. Moreover, the presence of harmful pathogens, like *Serratia marcescens*, exacerbates the risk, as they can lead to urinary tract infections, ocular lens infections, endocarditis, osteomyelitis, septicemia, and various other infections upon exposure.

While there have been attempts to address this issue through alternative proposals, such solutions often fall short in providing a comprehensive remedy. Surface treatments and sealants, for instance, may offer temporary relief by reducing water retention and inhibiting microbial growth. However, these treatments are susceptible to wear and degradation over time, necessitating frequent reapplication and maintenance. Furthermore, mechanical solutions, such as redesigned faucet structures or improved drainage systems, may alleviate some aspects of the problem but often fail to effectively address bacterial growth in hard-to reach areas.

SUMMARY OF THE INVENTION

Aspects of the invention provide a solution for illuminating and/or treating a surface area, such as horizontal surfaces, on or near a faucet, as described herein.

Embodiments provide surface treatment using ultraviolet light. The ultraviolet light can comprise, for example, ultraviolet-C (UVC) light.

Embodiments can use a light source in conjunction with a photocatalyst. For example, embodiments can use a combination of ultraviolet-A (UVA) light and a photocatalyst, such as titanium dioxide ($TiO_2$).

To ensure safe usage, embodiments can include a proximity sensor, which can be used to turn on and/or off the system.

Overall, embodiments of a solution described herein can provide a comprehensive safe, effective, and convenient solution for surface treatment, which can be customized to meet specific user needs.

Embodiments provide visible light illumination of the area, which can provide accent, safety, decorative, etc., light.

When combined with ultraviolet light, the visible light can provide information on the operation of the ultraviolet light sources, and/or the like.

Aspects of the invention provide mounting hardware for a faucet including one or more light sources for illumination. The light source(s) can be configured to emit light from one or more vertically oriented surfaces of the mounting hardware. One or more sensors can acquire sensor data that can be used to control operation of the light source(s). The light sources can include visible and/or ultraviolet light sources. When included, the ultraviolet light can be directed onto one or more areas of one or more horizontally oriented surfaces located adjacent to the vertically oriented surface(s). The light sources can be located in an escutcheon of the mounting hardware.

A first aspect of the invention provides a faucet comprising: a spout; an actuator configured to regulate a flow of water out of the spout; mounting hardware configured to mount the spout and the actuator to a horizontally oriented surface; at least one light source configured to emit light from at least one vertically oriented surface of the mounting hardware; and at least one sensor configured to acquire sensor data, wherein operation of the at least one light source is controlled based on the sensor data.

A second aspect of the invention provides mounting hardware for a faucet, the mounting hardware comprising: at least one visible light source configured to emit visible light; at least one ultraviolet light source configured to emit ultraviolet light from at least one vertically oriented surface of the mounting hardware directed onto at least one area of at least one horizontally oriented surface located adjacent to the at least one vertically oriented surface; at least one sensor configured to acquire sensor data; and a computing unit configured to operate the at least one visible light source and the at least one ultraviolet light source based on the sensor data.

A third aspect of the invention provides an escutcheon, comprising: at least one ultraviolet light source configured to emit ultraviolet light from at least one vertically oriented surface of the mounting hardware directed downward onto at least one area of at least one horizontally oriented surface located adjacent to the at least one vertically oriented surface; at least one sensor configured to acquire sensor data; and a computing unit configured to operate the at least one ultraviolet light source based on the sensor data.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
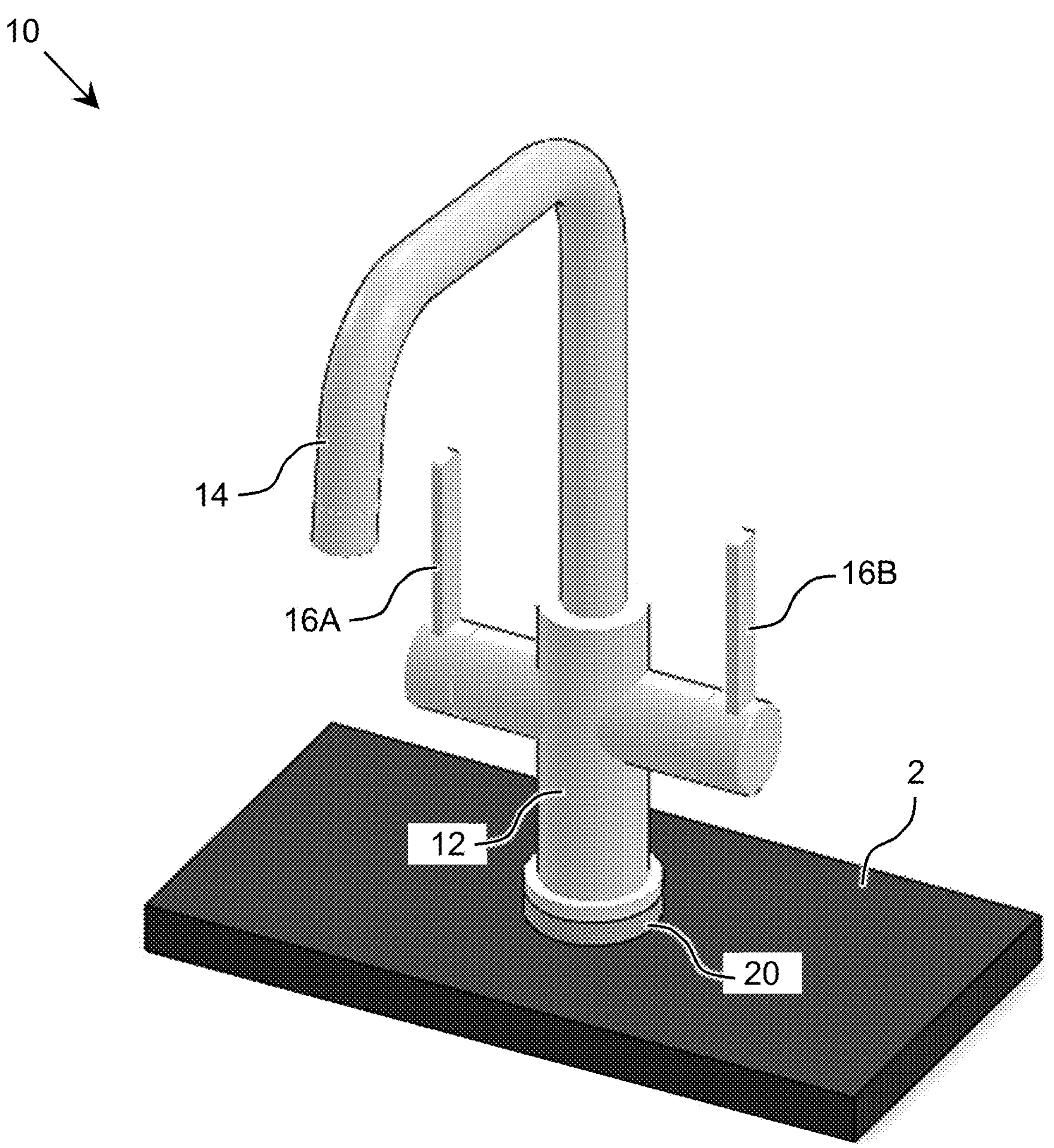
FIGS. 1A and 1B show an illustrative faucet according to embodiments.

As discussed herein, embodiments provide a faucet that includes visible light and/or ultraviolet light technologies. Embodiments of the faucet can enhance the aesthetic appeal of the faucet, provide practical functionality in addressing mold and bacterial growth, and/or the like. Incorporation of visible lighting can add a visually appealing element to the faucet, illuminate a surrounding area, thereby creating a warm and inviting atmosphere in the corresponding location, such as a kitchen or bathroom.

Embodiments of the ultraviolet light can include UV-C light, which is well-documented for its germicidal properties, effectively killing bacteria, viruses, and other pathogens upon exposure. By positioning the ultraviolet light emission near an interface between the faucet and a surface, such as the countertop, embodiments can effectively eliminate bacterial contamination, thus ensuring improved hygiene and user safety. Embodiments of the ultraviolet light can be used in conjunction with a photocatalyst to provide disinfection.

In embodiments, a faucet can incorporate a slender, transparent LED strip running along a generally vertically oriented edge where the faucet is mounted to the countertop. The LED strip can enhance the aesthetic appeal of the faucet and provide functional ambient lighting for the surrounding area. In embodiments, the LEDs used are energy-efficient and long-lasting, ensuring reliable performance and minimal maintenance requirements. The UV sources can be positioned discreetly within the faucet structure, and can be configured to emit, for example, short-wavelength UV-C light, known for its germicidal properties. This UV-C light effectively destroys the DNA of microorganisms, including mold spores, bacteria, and viruses, thereby preventing their proliferation and ensuring a hygienic environment around the faucet.

Embodiments can provide regular, automated disinfection without the need for manual intervention at interfaces between the faucet and a flat surface. Such locations are susceptible to standing water, which can promote the growth of microorganisms over time. Unlike traditional approaches, such as chemical treatments or surface coatings, which may offer temporary relief but require frequent reapplication and maintenance, embodiments can include an ultraviolet LED illumination component which can provide ongoing protection against microbial contamination, which can ensure long-term hygiene and minimize the risk of cross-contamination, particularly in high-traffic areas like kitchens and bathrooms.

Embodiments also can include one or more sensors, which can acquire data used to operate the visible and/or ultraviolet illumination, thereby enhancing the safety and usability of the faucet. A non-exhaustive list of sensors includes proximity sensors, such as light and/or motion detectors, which can detect the presence of users in the vicinity of the faucet. When human presence is detected, embodiments can automatically deactivate the UV LEDs, which can prevent any potential inadvertent exposure to UV-C radiation. This safety feature mitigates the risk of UV-related health hazards and ensures user confidence in the faucet's operation.

Furthermore, embodiments can be implemented in commercial environments, where mold prevention and hygiene are critical concerns. For example, in commercial kitchens, healthcare facilities, public restrooms, etc., embodiments of the faucet can be implemented to reduce the possible transmission of pathogens, enhance cleanliness, safety, and/or user experience across different industries and applications.

Embodiments provide a faucet including a faucet assembly and an integrated illumination system. The faucet assembly can comprise standard components such as the spout, handles, mounting hardware, etc. The integrated illumination system can be incorporated into a component of the faucet, or embodied as a component configured for use with the faucet. In either case, embodiments of the illumination system can be configured to provide both aesthetic appeal and functional benefits.

Embodiments of the illumination system can include a transparent LED strip positioned along an edge where a faucet component interfaces with a horizontal surface, such as a countertop. The strip can be powered by an energy-efficient driver and controlled by a microcontroller, which can operate the LEDs to provide uniform and aesthetically pleasing illumination for the interface area.

Embodiments of the illumination system can be discreetly integrated within the faucet structure. More particular embodiments can be configured to emit ultraviolet light, such as UV-C light, towards the interface between the faucet and the horizontal surface to prevent microbial growth. Embodiments can be powered by a dedicated driver and controlled by a microcontroller to ensure effective disinfection without compromising the faucet's functionality. Alternative configurations, such as distributing multiple illumination components throughout the faucet structure can provide enhanced disinfection coverage.

Embodiments can include safety sensors, such as proximity sensors, which can be strategically placed for use in conjunction with the faucet and illumination system, e.g., to detect human presence and trigger the deactivation of the UV LED system when users are detected. These sensors, which are communicatively connected to the microcontroller, can increase user safety and minimize the risk of UV-related health hazards. Additional sensor configurations, such as incorporating light sensors, temperature sensors, and/or the like, may be utilized to further augment safety measures and/or add other functionality to the system. Embodiments can use sensors currently embedded in a faucet. For example, a faucet may include a sensor that enables touchless operation of the faucet. Such sensor data can be used to operate the illumination system.

Embodiments of the faucet and illumination system described herein can be installed using standard plumbing techniques and tools. Additionally, embodiments can comprise retrofit kits for modifying an existing faucet installation, modular components for customizable configurations, and/or the like, which can accommodate various installation requirements and preferences.

Figure 1B:
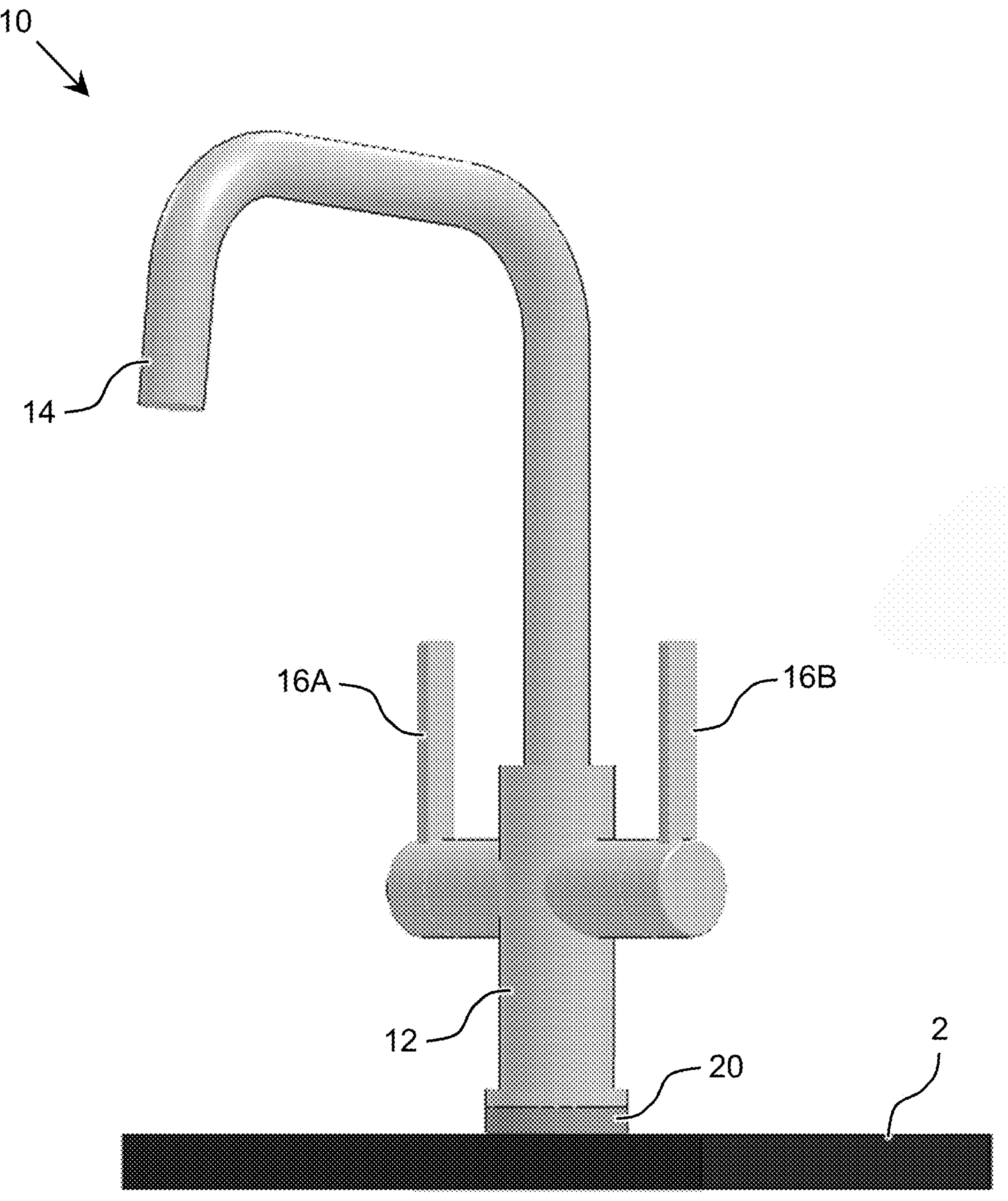

Turning to the drawings, FIGS. 1A and 1B show an illustrative faucet 10 according to embodiments. The faucet 10 includes a body 12 which is mounted to a horizontally oriented surface 2, such as a countertop, and which includes various components that enable the selective flow of water out of a spout 14. In this embodiment, the flow of water is regulated by one or more handles 16A, 16B, each of which can be utilized to selectively operate a valve in order to adjust the flow of hot and/or cold water as is well known in the art. However, it is understood that faucet 10 is only illustrative of various types of faucets and configurations thereof that can be implemented in embodiments. To this extent, embodiments of the faucet 10 can include one or more of any type of actuators, each of which is configured to operate a corresponding valve, including only one handle, one or more sensors that enable touchless (e.g., motion activated, voice operated, and/or the like) operation of valve(s), one or more sensors that enable touch operation (e.g., on the spout 14) of valve(s), etc.

The faucet 10 also includes an illumination component 20. In embodiments, the illumination component 20 is implemented within an escutcheon, which can be configured to provide an ornamental and/or protective covering around an opening in the surface 2 through which the plumbing components of the faucet 10 extend. To this extent, the escutcheon 20 can provide an interface between the faucet 10 and the surface 2. In embodiments, the escutcheon 20 includes an illumination component described herein, which can provide illumination, such as decorative or soft illumination, of an area around the escutcheon 20. In embodiments, the escutcheon 20 includes a surface treatment system described herein, which can be configured to treat an area of the surface 2 in the immediate vicinity of the escutcheon 20.

In embodiments, the escutcheon 20 can be provided as a component of the faucet 10. In other embodiments, the escutcheon 20 can be provided as a replacement to a component of the faucet 10. In still other embodiments, the escutcheon 20 can be provided as a component that is configured to be placed and used in conjunction with a faucet 10. For example, the escutcheon 20 can be configured to be secured to an outer surface of an existing faucet, without modification to the existing faucet. In more particular embodiments, the escutcheon 20 can be implemented as a slender, transparent LED strip, which is secured to an outer surface of a faucet and/or its escutcheon.

Figure 2A:
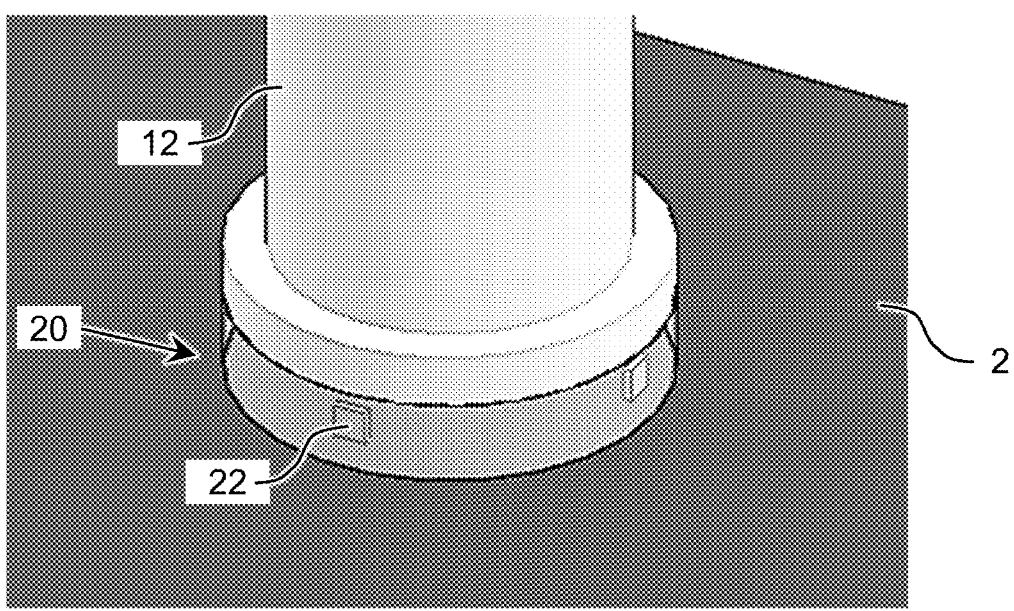
FIGS. 2A and 2B show illustrative escutcheons according to embodiments.
Figure 2B:
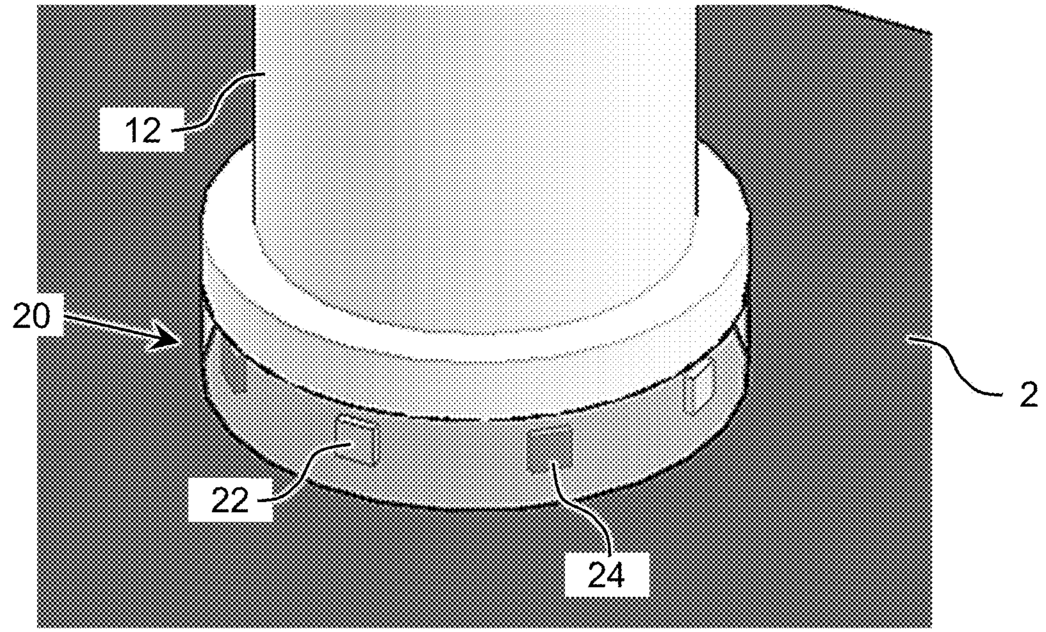

FIGS. 2A and 2B show more detailed views of illustrative escutcheons 20 according to embodiments. As illustrated in FIG. 2A, embodiments of the escutcheon 20 can include one or more light sources 22, which can be configured to emit light from one or more locations on the perimeter of the escutcheon 20. In embodiments, the light sources 22 can emit visible light. In embodiments, the visible light can be perceived as white light or light perceived as having another color, such as blue, red, green, yellow, violet, orange, etc. In embodiments, the light sources 22 can be configured to selectively emit, concurrently and/or at different times, light perceived as two or more different colors. In embodiments, the light sources 22 can be manually operated, operated by a computing unit, operated in response to sensor data, and/or the like.

As illustrated in FIG. 2B, embodiments of the escutcheon 20 can include one or more ultraviolet light sources 24, which can be configured to emit ultraviolet light from one or more locations on the perimeter of the escutcheon 20. Embodiments of the ultraviolet light source 24 can include one or more ultraviolet light emitting diodes, one or more mercury-based lamps, one or more fluorescent lamps, and/or the like. In embodiments, the escutcheon can include light guiding structures, such as optical fibers and/or the like, which can direct light emitted from an ultraviolet light source 24 to one or more locations located on an external surface of the escutcheon 20 from which the ultraviolet light is emitted.

In embodiments, the ultraviolet light sources 24 emit light within one or more subsets of the ultraviolet light range of wavelengths. In embodiments, the ultraviolet light comprises ultraviolet-C light, which has a peak wavelength in a range between 100 nanometers and 280 nanometers. In this case, the ultraviolet light can be configured to kill or inactivate microorganisms that may be present on the surface 2. In embodiments, the ultraviolet light comprises ultraviolet-A light, which has a peak wavelength in a range between 315 nanometers and 400 nanometers. Such ultraviolet light can be used to suppress growth, activate a photocatalyst, and/or the like.

In embodiments, the ultraviolet light sources 24 can be configured to selectively emit, concurrently and/or at different times, ultraviolet radiation within two or more subsets of the ultraviolet light range of wavelengths. In embodiments, the ultraviolet light sources 24 can be manually operated, operated by a computing unit, operated in response to sensor data, and/or the like.

As also illustrated in FIG. 2B, embodiments of the escutcheon 20 can include both one or more light sources 22 and one or more ultraviolet light sources 24. In embodiments, the respective sources 22, 24 can be independently operated and/or operated together. In embodiments, the light sources 22 can be operated to provide a visual indication of an operating status of the ultraviolet light sources 24.

In embodiments, light emitted from the light sources 22, 24 is diffuse. Embodiments can include light sources 22, 24 configured to provide a relatively constant illumination flux about an entire perimeter of the escutcheon 20. For example, embodiments of the light sources 22, 24 can provide illumination in which the flux varies by no more than 25% about the perimeter of the escutcheon 20.

Embodiments of the escutcheon 20 can be implemented separately from the body 12 of the faucet 10. Embodiments of the escutcheon 20 can be sized, shaped, and fabricated from a material that is configured to provide the same aesthetic appearance as a standard escutcheon for the faucet 10, which can be replaced with the escutcheon 20. As illustrated, embodiments of the escutcheon 20 can have a size and shape approximately similar to that of the body 12. However, it is understood that this configuration is only illustrative. In embodiments, the escutcheon 20 can have any of various sizes, shapes, etc., which can selectively vary based on a location and configuration of the handle(s) 16A, 16B, spout 16, a size and number of openings to be covered in the surface 2, etc.

In embodiments, the illumination system can be implemented within a multisided structure. In embodiments, the illumination system can be implemented as part of the mounting hardware for the faucet 10. To this extent, FIGS. 3A and 3B show top and front angle views of illustrative mounting hardware including the illumination system 20 according to embodiments.

Figure 3A:
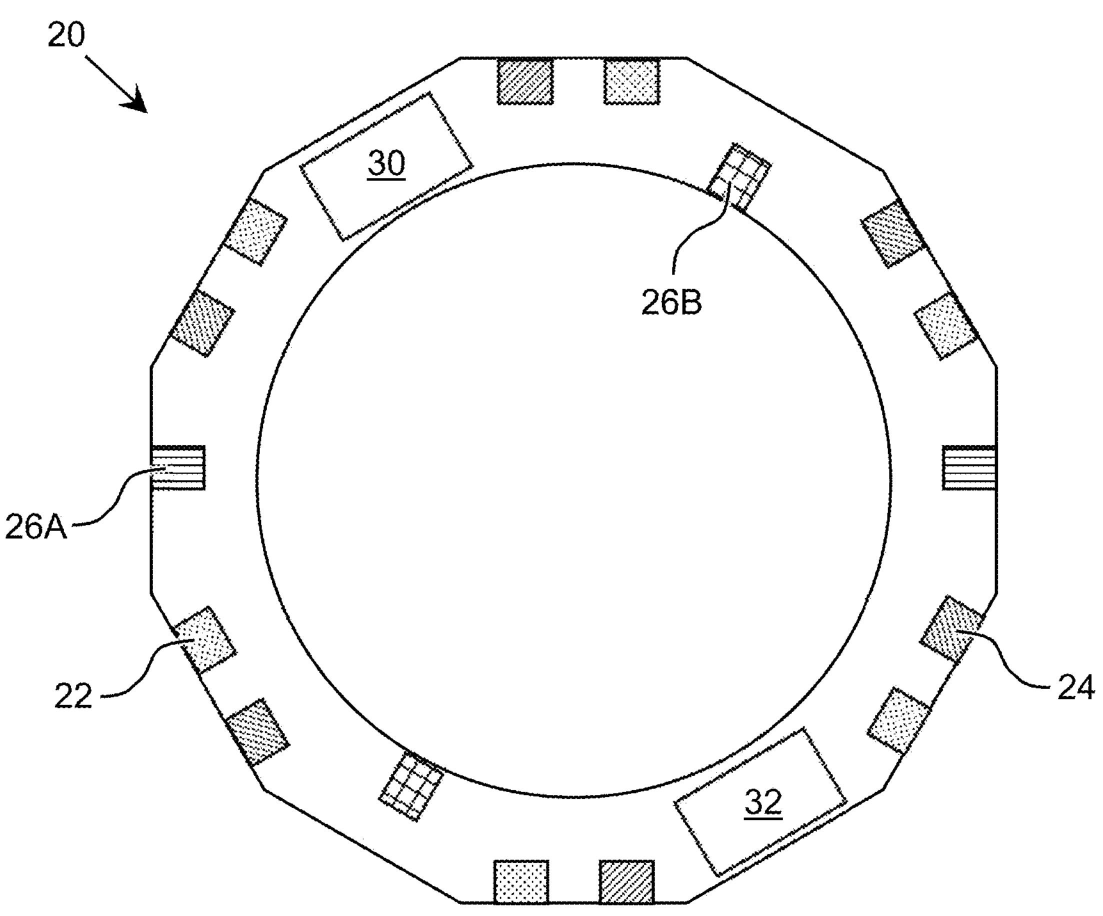
FIGS. 3A and 3B show illustrative mounting hardware according to embodiments.

As illustrated in FIG. 3A, the mounting hardware 20 can include multiple sides (e.g., twelve are illustrated), which can facilitate securing a faucet to a mounting surface using the mounting hardware 20. For example, as illustrated in FIG. 3B, the mounting hardware 20 can included a threaded opening that allows the mounting hardware 20 to be secured to a corresponding threaded pipe or the like for the faucet.

Regardless, the mounting hardware 20 can include an illumination component described herein embedded therein.

Figure 3B:
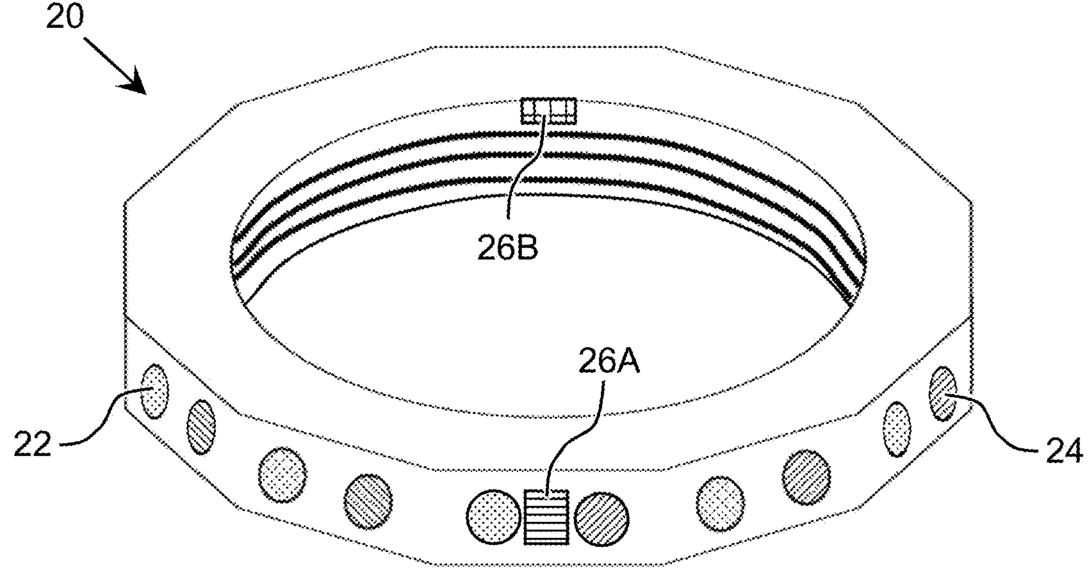

To this extent, the mounting hardware 20 shown in FIGS. 3A and 3B is shown including various visible light sources 22 and ultraviolet light sources 24, which are configured to emit light outward from one or more of the external sides of the mounting hardware 20. As illustrated in FIGS. 3A and 3B, some or all of the external surfaces of the mounting hardware 20 can include one or more visible light sources 22 and/or one or more ultraviolet light sources 24. While the visible and ultraviolet light sources 22, 24 are shown located in pairs, it is understood that this is only illustrative and any arrangement can be implemented.

FIGS. 3A and 3B also illustrate the inclusion of various additional components of the illumination system within the mounting hardware 20, which also can be included in an escutcheon described herein. For example, the illumination system also can include one or more sensors, which can acquire data used in the operation of the visible and/or ultraviolet light sources 22, 24, a computing unit for controlling the operation, a power source, etc.

To this extent, the mounting hardware 20 is illustrated as including a set of sensors 26A located on one or more of the external sides of the mounting hardware 20. In embodiments, the set of sensors 26A can include one or more sensors configured to detect an amount of ambient light. Data acquired by a light sensor can be used to operate the visible light sources 22, for example. In embodiments, the set of sensors 26B can include one or more proximity sensors, which can detect a presence of a person in a vicinity of the faucet. Data acquired by a proximity sensor can be used in operation of the visible and/or ultraviolet light sources 22, 24. It is understood that these sensors are only illustrative of various sensors that can be implemented as part of an illumination system described herein.

Additionally, the mounting hardware 20 is illustrated as including a set of sensors 26B located on an internal surface of the mounting hardware 20. In embodiments the set of sensors 26B can include a sensor configured to acquire data corresponding to a flow of water through the faucet. For example, a sensor 26B can comprise a vibration sensor, which can acquire data corresponding to vibrations caused by water flowing through the faucet. Data corresponding to the flow of water through the faucet can be used in operation of the visible and/or ultraviolet light sources 22, 24.

The mounting hardware 20 also is shown including a computing unit 30, which can be configured to control operation of the visible and/or ultraviolet light sources 22, 24, e.g., using data received from the sensors 26A, 26B. The computing unit 30 can comprise any type of computing unit capable of controlling operation of one or more input and/or output devices in order to illuminate (e.g., for lighting and/or treatment) an area around the faucet. Embodiments of the computing unit 30 can include a programmable computer (e.g., including one or more processors, memory, and I/O interfaces) executing program code installed thereon, one or more special purpose microprocessors, and/or the like.

In embodiments, the computing unit 30 comprises one or more real-time controllers (RTCs). The RTC(s) can enable programmable scheduling of visible illumination and/or UV treatment cycles based on, for example, user preferences, usage patterns, etc. For example, UV treatment can be scheduled during periods of low human activity, such as late at night or early morning, e.g., to maximize effectiveness while minimizing disruption to users. UV treatment also can be scheduled to occur only after use of the faucet, after a predetermined number of uses of the faucet, after a predetermined volume of liquid flowing through the faucet, after a predetermined time from a previous treatment, and/or the like. Embodiments of the faucet can incorporate scheduled treatment periods to provide for energy reduction, extended operating lifetime of the illumination system, maintaining optimal operating temperatures, etc. However, it is understood that embodiments can provide persistent operation, which can ensure continuous disinfection, e.g., in environments where microbial contamination is a persistent concern.

The computing unit 30 can be configured to operate the visible and/or ultraviolet light sources 22, 24 using any solution. For example, after use of the faucet 10, the computing unit 30 can turn on the ultraviolet light sources 24 for a predetermined period of time to deliver a desired dose of ultraviolet light to the surface 2. In embodiments, the computing unit 30 waits for a period of time after use of the faucet 10 prior to turning on the ultraviolet light sources 24, e.g., to provide time for any moisture to dry. In embodiments, the computing unit 30 can turn on the visible light sources 22 in response to detecting a low amount of ambient light, detecting the presence of a person, and/or the like.

The computing unit 39 can operate the ultraviolet light source 24 in any manner to deliver a desired dose of ultraviolet light to the surface 2. For example, the computing unit 30 can operate the ultraviolet light source 24 to generate ultraviolet light in a pulsed manner, continuously, for multiple predetermined periods of time separated by predetermined periods of time when the ultraviolet light sources are off, and/or the like.

Inclusion of RTCs or similar computing units, can enable the timing of UV-based treatment based on user preferences, usage patterns, and/or the like. Embodiments of the RTCs can be programmable with predefined schedules and/or user-configurable settings, which can provide automated and/or customizable control over treatment cycles. While embodiments can provide alternative control methods, such as manual switches, remote control options, etc., inclusion of RTCs or similar computing units can provide a more efficient and user-friendly solution for managing disinfection operations.

Additionally, the mounting hardware 20 is shown including a power component 32. The power component 32 can comprise any type of power source. For example, the power component 32 can comprise one or more batteries, an electrical plug and transformer for obtaining power from an electrical receptacle, and/or the like. Regardless, the power component 32 can be configured to provide sufficient power to operate the remaining components of the illumination component. In embodiments, the power component 32 can comprise a rechargeable battery, which can be recharged using a wireless charging solution, using the flow of the water through the faucet, using ambient light, and/or the like.

As described herein, the illumination component can be configured to treat an area of a surface located near the faucet in order to prevent, suppress, etc., mold growth and the like. In embodiments, the illumination component can be configured to treat a surface area of the faucet itself, which also may be susceptible to such growth.

Figure 4A:
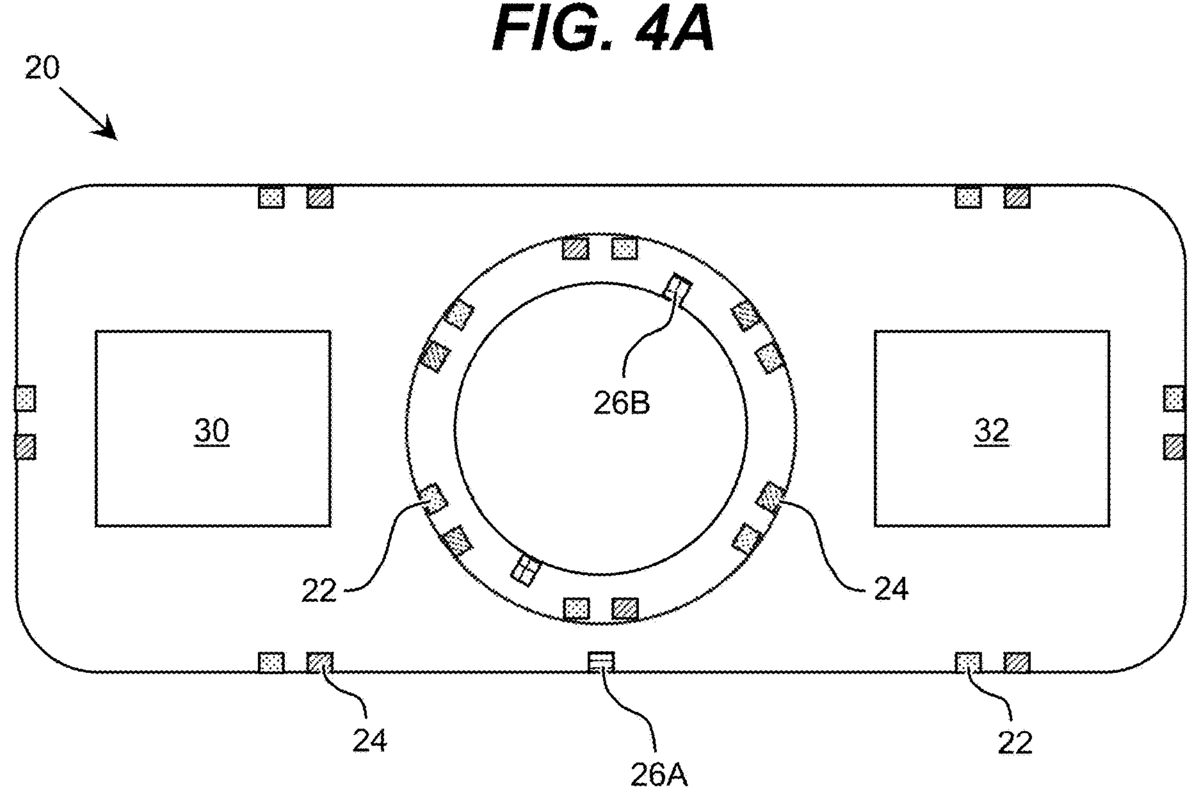
FIGS. 4A and 4B show illustrative escutcheons according to embodiments.
Figure 4B:
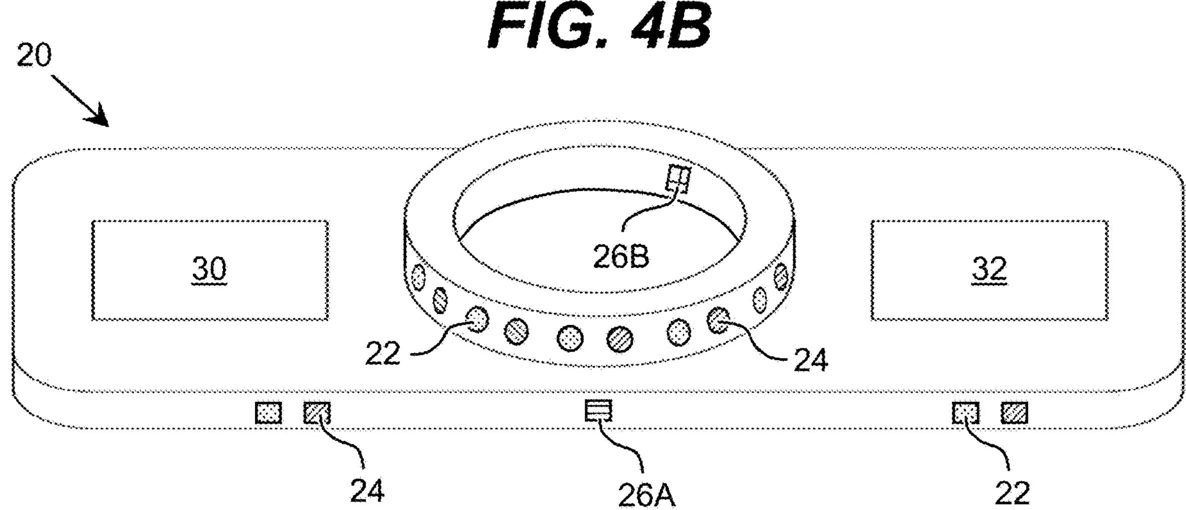

To this extent, FIGS. 4A and 4B show illustrative escutcheons 20 including an illumination system described herein according to embodiments. In this case, the escutcheons 20 include a raised central housing, through which plumbing for the faucet can extend, and a larger rectangular structure surrounding the central housing. While not shown, it is understood that escutcheons 20 also can include more than one opening, e.g., to facilitate mounting of handles or the like directly thereon.

Regardless, the escutcheons 20 are shown including visible 22 and ultraviolet light sources 24, which are configured to emit visible and ultraviolet light, respectively, from various locations around the central housing as well as around the perimeter of the escutcheons 20. While visible and ultraviolet light sources 22, 24 are shown to illuminate both of the areas, it is understood that various alternative configurations are possible. For example, the visible light sources 22 may be included in only one of the locations on the escutcheons 20.

As illustrated, embodiments of the escutcheon 20 can include an external sensor 26A, which can be configured to determine whether any individual is present in an area close to the faucet. In embodiments, the escutcheon 20 can be configured to be installed such that one side is a front side, which faces a direction of the user. In this case, embodiments of the escutcheon 20 can include an external sensor 26A located only on the front side. While the external sensor 26A is shown mounted to the bottom plate, it is understood that the external sensor 26A could be mounted to the central structure instead. Additionally, embodiments can include an external sensor 26A which is located physically apart from the escutcheon 20, e.g., integrated into a wall, another component of the faucet, a ceiling, and/or the like, which can provide data corresponding to the presence of an individual using a wireless solution.

In embodiments, the visible and/or ultraviolet light sources 22, 24 can comprise light emitting diodes or the like, which are configured to emit light out of the corresponding structure (e.g., mounting hardware, escutcheon, etc.). In embodiments, the visible and/or ultraviolet light sources 22, 24 can be mounted in recesses formed in the corresponding structure, which can be configured to direct light emitted by the visible and/or ultraviolet light sources 22, 24 away from the structure.

Figure 5A:
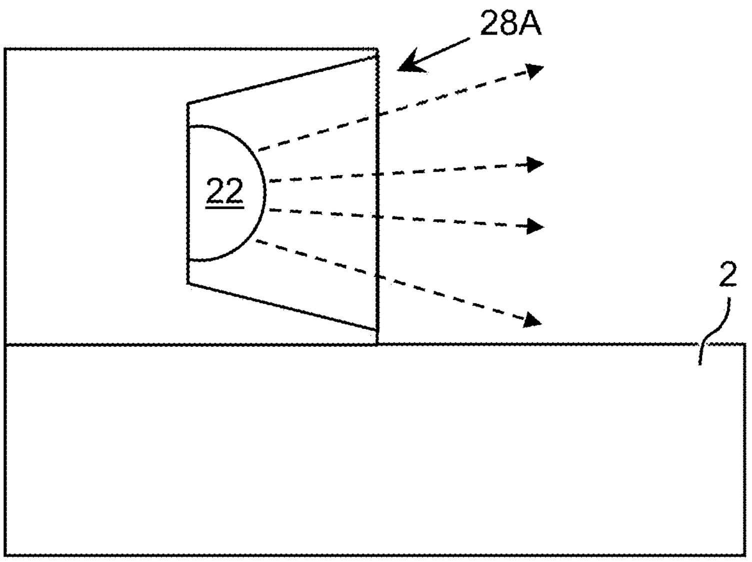
FIGS. 5A and 5B show illustrative light source configurations according to embodiments.
Figure 5B:
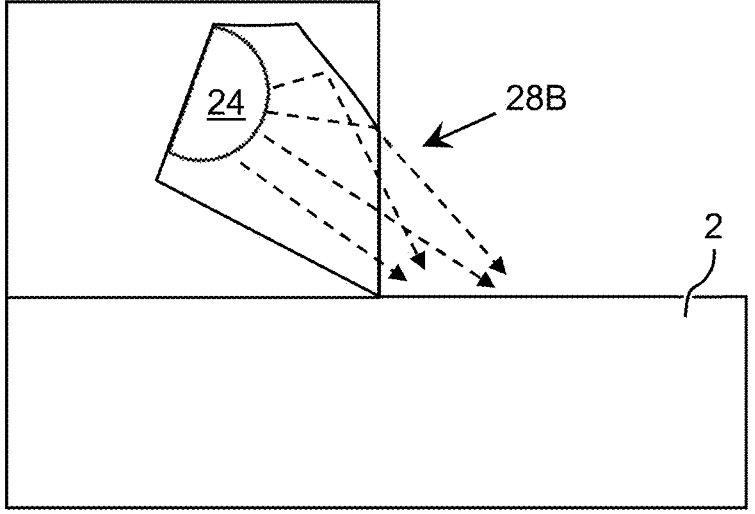

FIGS. 5A and 5B show illustrative light source configurations according to embodiments. As illustrated, each light source 22, 24 can be mounted within a recess 28A, 28B, respectively. For the visible light source 22, embodiments of the recess 28A can be configured to allow emission of light away from the structure in any of various directions.

For the ultraviolet light source 24, embodiments of the recess 28B can be configured to direct the ultraviolet light downward towards the surface 2. Such an illumination can prevent ultraviolet light from being directed toward an individual or another object, which may be in the vicinity of the area of the surface 2 to be treated. It is understood that any of various solutions can be used to direct the ultraviolet light to only impact an area located near the structure. For example, the solutions can include mounting the ultraviolet light source 24 at a downward angle, using one or more reflective surfaces to direct the ultraviolet light downward, using one or more surfaces to prevent the ultraviolet light from exiting the recess 28B in a direction going away or parallel with the surface 2, etc. In embodiments, the recesses 28A, 28B can be filled with a transparent material to protect the corresponding light sources 22, 24 from contamination. Illustrative materials include fused quartz, UVC silicones, clear acrylic, and/or the like. In embodiments, an external surface of the transparent material can include surface roughening and/or the like, which can cause, for example, visible light, to be scattered in different directions after passing through the surface.

It is understood that while not shown for clarity, the various illumination systems described herein can include wiring and other components that enable communication and/or power connectivity between the various components.

In embodiments, a surface to be illuminated by an ultraviolet light source can be treated in order to prevent the surface from being damaged by the ultraviolet light and/or with a material that is used in conjunction with the ultraviolet light. For example, a surface can be coated with photocatalyst, such as a titanium dioxide coating, which can work in conjunction with ultraviolet A light in order to treat an area. Additionally, ultraviolet stabilizers or blockers can be used to absorb or reflect UV rays, thereby protecting surfaces from UV-induced degradation like color fading or material weakening. Selection of an appropriate coating depends on factors like application specifics and environmental conditions. For example, many countertops, such as those fabricated from granite, are currently treated with sealants to protect against stains and moisture. Embodiments can use UV-resistant sealants and/or photocatalytic sealants for such countertops. UV-resistant sealants are formulated to withstand UV exposure and maintain their protective properties.

Figure 6:
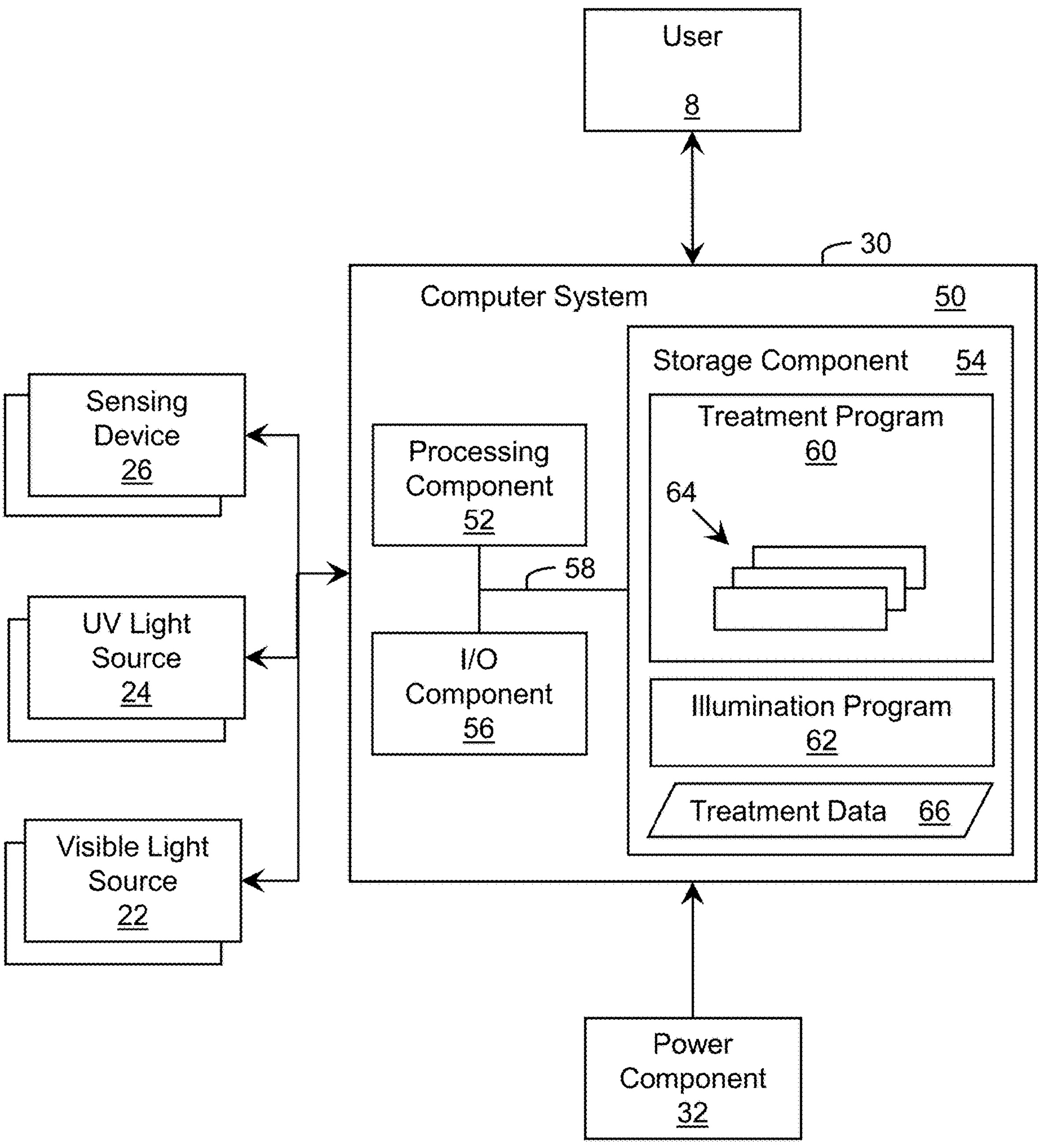
FIG. 6 shows a schematic of an illustrative surface treatment system according to an embodiment.

FIG. 6 shows a schematic of an illustrative illumination system according to an embodiment. To this extent, the illumination system includes a computing unit 30, which is implemented as a computer system 50 that can perform a process described herein in order to illuminate an area around a faucet. In particular, the computer system 50 is shown including a treatment program 60, which makes the computer system 50 operable to treat an area by performing a process described herein. Furthermore, the computer system 50 is shown including an illumination program 62, which makes the computer system 50 operable to illuminate an area around the faucet by performing a process described herein.

The computer system 50 is schematically illustrated as including a processing component 52 (e.g., one or more processors), a storage component 54 (e.g., a storage hierarchy), an input/output (I/O) component 56 (e.g., one or more I/O interfaces and/or devices), and a communications pathway 58. In general, the processing component 52 executes program code, such as the treatment program 60 and/or the illumination program 62, which is at least partially fixed in storage component 54. While executing program code, the processing component 52 can process data, which can result in reading and/or writing transformed data from/to the storage component 54 and/or the I/O component 56 for further processing. The pathway 58 provides a communications link between each of the components in the computer system 50.

The I/O component 56 can comprise one or more human I/O devices, which enable a human user 8 to interact with the computer system 50 and/or one or more communications devices to enable a system user 8 (e.g., a portable computing device of a human user, such as a mobile phone executing an app) to communicate with the computer system 50 using any type of communications link. To this extent, the treatment program 60 and/or illumination program 62 can manage a set of interfaces (e.g., graphical user interface(s), application program interface, and/or the like) that enable human and/or system users 8 to interact with the treatment program 60 and the treatment data 66, the illumination program 62, etc. Furthermore, the treatment program 60 can manage (e.g., store, retrieve, create, manipulate, organize, present, etc.) the treatment data 66 using any solution.

In any event, the computer system 50 can comprise one or more general purpose computing articles of manufacture (e.g., computing devices) capable of executing program code, such as the treatment program 60 and/or illumination program 62, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the treatment program 60 can be embodied as any combination of system software and/or application software.

Furthermore, the treatment program 60 and/or illumination program 62 can be implemented using a set of modules 64. In this case, a module 64 can enable the computer system 50 to perform a set of tasks used by the treatment program 60 and/or illumination program 62, and can be separately developed and/or implemented apart from other portions of the treatment program 60 and/or illumination program 62. As used herein, the term "component" means any configuration of hardware, with or without software, which implements the functionality described in conjunction therewith using any solution, while the term "module" means program code that enables a computer system 50 to implement the actions described in conjunction therewith using any solution. Regardless, it is understood that two or more components, modules, and/or systems may share some/all of their respective hardware and/or software. Furthermore, it is understood that some of the functionality discussed herein may not be implemented or additional functionality may be included as part of the computer system 50.

When the computer system 50 comprises multiple computing devices, each computing device can have only a portion of the treatment program 60 and/or illumination program 62 fixed thereon (e.g., one or more modules 64). In embodiments, the computer system 50 can comprise a computing unit located within a component of the faucet and a portable computing unit, such as a mobile phone, which is executing an app installed thereon for enabling a user 8 to monitor, evaluate, manage, and/or the like, the illumination system.

However, it is understood that the computer system 50 and the treatment program 60 and/or illumination program 62 are only representative of various possible equivalent computer systems that may perform a process described herein. To this extent, in other embodiments, the functionality provided by the computer system 50 and the treatment program 60 and/or illumination program 62 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 50 includes multiple computing devices, the computing devices can communicate over any type of communications link. Furthermore, while performing a process described herein, the computer system 50 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

As also used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer. In an embodiment, the target wavelength of the radiation corresponds to a wavelength of radiation emitted or sensed (e.g., peak wavelength+/− five nanometers) by an active region of an optoelectronic device during operation of the device. For a given layer, the wavelength can be measured in a material of consideration and can depend on a refractive index of the material.

It is understood that, unless otherwise specified, each value is approximate and each range of values included herein is inclusive of the end values defining the range. Terms of degree such as "generally," "substantially," "about," and "approximately" as used herein mean a reasonable amount of deviation of the modified term such that the end result is not significantly changed. For example, these terms can be construed as including a deviation of at least +/−0.5% of the modified term if this deviation would not negate the meaning of the word it modifies. In a more particular example, the term "approximately" is inclusive of values within +/− ten percent of the stated value, while the term "substantially" is inclusive of values within +/− five percent of the stated value when these deviations would not negate the meaning of the word each term modifies. Unless otherwise stated, two values are "similar" when the amount of deviation between the two values does not significantly change the result. In a more particular example, two values are similar when the smaller value is within +/− twenty-five percent of the larger value. A value, y, is on the order of a stated value, x, when the value y satisfies the formula $0.1x \leq y \leq 10x$.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A faucet comprising:

a spout;

an actuator configured to regulate a flow of water out of the spout;

mounting hardware configured to mount the spout and the actuator to a horizontally oriented surface;

at least one light source configured to emit light from at least one vertically oriented surface of the mounting hardware;

at least one sensor configured to acquire sensor data, wherein operation of the at least one light source is controlled based on the sensor data; and a surface treatment component configured to operate the at least one light source in order to treat at least one area of at least one horizontally oriented surface located adjacent to the at least one vertically oriented surface, wherein the at least one light source includes at least one ultraviolet light source.

2. The faucet of claim 1, wherein the mounting hardware includes an escutcheon, and wherein the at least one vertically oriented surface is located on the escutcheon.

3. The faucet of claim 1, further comprising an illumination component configured to operate the at least one light source, wherein the at least one light source includes a visible light source, and wherein the at least one sensor includes a light sensor configured to acquire sensor data corresponding to an amount of ambient light.

4. The faucet of claim 1, wherein the at least one sensor includes a proximity sensor configured to acquire sensor data regarding a presence of a person.

5. The faucet of claim 4, wherein the at least one ultraviolet light source is configured to emit ultraviolet-C light.

6. The faucet of claim 4, wherein light emitted from the least one ultraviolet light source is directed downward towards the at least one area of the at least one horizontally oriented surface.

7. The faucet of claim 4, wherein the at least one light source includes at least one visual light source, and wherein the surface treatment component is configured to operate the at least one visual light source to indicate an operating status of the at least one ultraviolet light source.

8. The faucet of claim 1, wherein the at least one sensor includes at least one flow sensor configured to acquire sensor data regarding a flow of water through the faucet.

9. The faucet of claim 1, wherein the mounting hardware includes a computing unit configured to operate the at least one light source based on the sensor data.

10. The faucet of claim 9, wherein the mounting hardware further includes a power component configured to provide power to the computing unit.

11. The faucet of claim 1, wherein at least one of the at least one sensor is located physically apart from the faucet.

12. Mounting hardware for a faucet, the mounting hardware comprising:

at least one visible light source configured to emit visible light;

at least one ultraviolet light source configured to emit ultraviolet light from at least one vertically oriented surface of the mounting hardware directed to treat at least one area of at least one horizontally oriented surface located adjacent to the at least one vertically oriented surface;

at least one sensor configured to acquire sensor data; and a computing unit configured to operate the at least one visible light source and the at least one ultraviolet light source based on the sensor data.

13. The mounting hardware of claim 12, wherein the mounting hardware comprises an escutcheon, wherein the at least one horizontally oriented surface is located adjacent to and/or on the escutcheon.

14. The mounting hardware of claim 12, wherein the at least one sensor includes a light sensor configured to acquire data corresponding to an amount of ambient light, and wherein the computing unit is configured to operate the at least one visible light source based on sensor data acquired by the light sensor.

15. The mounting hardware of claim 12, wherein the at least one sensor includes a proximity sensor configured to acquire sensor data regarding a presence of a person, and wherein the computing unit is configured to operate the at least one ultraviolet light source based on sensor data acquired by the proximity sensor.

16. The mounting hardware of claim 12, wherein the at least one sensor includes a flow sensor configured to acquire sensor data regarding a flow of water through the faucet, and wherein the computing unit is configured to operate the at least one ultraviolet light source based on sensor data acquired by the flow sensor.

17. The mounting hardware of claim 12, wherein light emitted from the least one ultraviolet light source is directed downward towards the at least one area of the at least one horizontally oriented surface.

18. An escutcheon, comprising:

at least one ultraviolet light source configured to emit ultraviolet light from at least one vertically oriented surface of the mounting hardware directed downward to treat at least one area of at least one horizontally oriented surface located adjacent to the at least one vertically oriented surface;

at least one sensor configured to acquire sensor data; and a computing unit configured to operate the at least one ultraviolet light source based on the sensor data.

19. The escutcheon of claim 18, wherein the at least one sensor includes a proximity sensor configured to acquire sensor data regarding a presence of a person, and wherein the computing unit is configured to operate the at least one ultraviolet light source based on sensor data acquired by the proximity sensor.

20. The escutcheon of claim 18, wherein the at least one sensor includes a flow sensor configured to acquire sensor data regarding a flow of water through a faucet, and wherein the computing unit is configured to operate the at least one ultraviolet light source based on sensor data acquired by the flow sensor.

* * * * *